United States Patent [19]

Harris et al.

[11] Patent Number: 4,874,949
[45] Date of Patent: Oct. 17, 1989

[54] METHOD OF MEASURING LUNG VASCULAR FUNCTION AND TRANSCAPILLARY TRANSPORT BY THE USE OF NONRADIOACTIVE MARKERS

[75] Inventors: Thomas R. Harris; Robert L. Galloway, Jr., both of Nashville, Tenn.

[73] Assignee: Vanderbilt University, Nashville, Tenn.

[21] Appl. No.: 96,856

[22] Filed: Sep. 14, 1987

[51] Int. Cl.$^4$ ............................................. G01N 21/35
[52] U.S. Cl. .................................. 250/343; 128/664; 250/302; 250/339; 250/345; 356/40; 364/413.09
[58] Field of Search ............... 250/302, 339, 345, 343, 250/349, 356.1; 356/40, 42; 364/416, 413.09; 128/633, 664, 667, 666, 665

[56] References Cited

U.S. PATENT DOCUMENTS 3,677,648  7/1972  Dorsch .................................. 356/40
4,569,589  2/1986  Neufeld ................................. 356/39

OTHER PUBLICATIONS

John A. Williams and James B. Williams, "Clinical Nuclear Instrument Measures Blood Volume", *Nucleonics*, vol. 20, No. 11 (Nov. 1962) pp. 63–64.
Georg Thieme, "Circulation Diagnostics", a translation from German (performed by the Harvard Translating & Editorial Service) of a document published in Stuttgart, Germany in 1962.
Basset, et al., "Simultaneous Detection of Deuterium Oxide and Indocyanine Green in Flowing Blood", *J. Appl. Physiol.*, 50:1367–1371 (1981).
Lewis, et al., "The Measurement of Extravascular Lung Water by Thermol. Green Dye Indicator Dilution", *Ann. NY Acad. Sci.*, 384:394–410 (1982).
Harris, et al., "The Exchange of Small Molecules as a Measure of Normal and Abnormal Lung Microvascular Function", *Ann. NY Acad. Sci.*, 384:417–434 (1982).
Harris, et al., "Exchange of Small Molecules in the Normal and Abnormal Lung Circulatory Bed" in *Respiratory Physiology: A Quantitative Approach*, Chang and Paiva, ed., Dekker, NY, in press (1987).
Harris, et al., "Comparison of Labeled Propanediol and Urea as Markers of Lung Vascular Injury", *J. Appl. Physiol.*, 62:1852–1859 (1987).
Parker, et al., "Effect of Perfusate Hematocrit on Urea Permeability–Surface Area in Isolated Dog Lung", *J. Appl. Physiol.*, 60:1383–1387 (1986).
Baker, et al., "Microvessel Mean Transit Time and Blood Flow Velocity of Sulfhemoglobin in RBC", *Am. J. Physiol.*, 238:H745–H749 (1980).
Kampen, et al., "Spectrophotometry of Hemoglobin and Hemoglobin Derivatives", *Adv. in Clin. Chem.*, 23:199–257 (1983).
Mook, et al., "Spectrophometric Determination of Oxygen Saturation of Blood Independent of the Presence of Indocyanine Green", *Cardiovascular Res.*, 13:233–237 (1979).
Brigham, et al., "Correlation of Oxygenation with Vascular Permeability–Surface Area but not with Lung Water in Humans with Acute Respiratory Failure and Pulmonary Edema", *J. Clin Invest.*, 72:339–349 (1983).
Roselli, et al., "Effects of Red Cell Exchange on Calculated Sheep Lung Vascular Permeability to $^{14}$C–Urea and $^{14}$C–Thiourea", *Respiration Physiol.*, 49:11–21 (1982).
Staton, et al., "Comparison of Sulfhemoglobin and $^{51}$Chromium as Red Blood Cell (RBC) Labels in Indicator–Dilution Curves", Abstract in *Pulmonary Circulation III: General*, #6319, p. 1399.

Primary Examiner—Constantine Hannaher
Attorney, Agent, or Firm—Tilton, Fallon, Lungmus & Chestnut

[57] ABSTRACT

Infrared sensitive indicator-dilution tracer concentration, specifically, 1,2 propanediol, can be optically measured in blood drawn from the systemic arterial system to indicate lung vascular function and transcapillary transport, i.e. pulmonary blood flow, extravascular lung water, transcapillary permeability-surface area, fluid filtration coefficients, etc. that may be helpful in diagnosing lung diseases, particularly Adult Respiratory Distress Syndrome (ARDS).

8 Claims, 8 Drawing Sheets

METHOD OF MEASURING LUNG VASCULAR FUNCTION AND TRANSCAPILLARY TRANSPORT BY THE USE OF NONRADIOACTIVE MARKERS

GRANT REFERENCE

This invention was developed under NIH Grant No. 2507RR07201-07 Biomedical Research Support.

BACKGROUND AND PRIOR ART

The present invention relates to indicator-dilution (or diffusion) principles of circulatory physiology. More specifically, the invention relates to a method of utilizing nonradioactive markers for measuring lung vascular function and transcapillary transport by optical methods and blood drawn from the systemic arterial system. The relative concentrations of the markers can be readily observed from their infrared and visible spectra in blood which will offer the immediate determination and display of parameters which characterize the lung vascular barrier and will be helpful in assessing lung diseases, such as adult respiratory distress syndrome (ARDS).

Indicator dilution methods based on green dye and other materials capable of absorbing visible light are well established for the measurement of cardiac output and oxygen content. Recently, these methods have been extended to the infrared spectrum by Basset et al. (1981) *J. Appl. Physiol.* 50:1367–1371 and Neufeld et al. (1983) *Proceedings 2nd Int. Symposium on Computing in Anesthesia in Intensive Care*, Rotterdam. These devices for measuring light transmittance of indocyanine green dye and deuterated water ($D_2O$) have been connected to microcomputers which calculate mean transit times, pulmonary blood flow and extravascular lung water from lung vascular indicator curves. Blood is withdrawn through an optical window and the transmittance of filtered light is detected electronically. This method relies on the high absorbance of ($D_2O$) to provide a sensitive and specific indicator of extravascular lung water. The method may be superior to clinical applications of the thermal green dye method of Lewis et al. (1982) *Ann. N. Y. Acad. Sci.* 384:394–410 in that it does not require an indwelling arterial probe. However, none of these methods can readily obtain microvascular permeability surface area (PS) measurements.

Other methods for evaluation of the microvascular properties of the lung include the multiple radioactive isotope method using $^{125}I$-albumin, $^{51}Cr$-red blood cells $^{14}C$-urea and $^3H$-water. See Harris, et al. (1982) *Ann. N.Y. Acad. Sci.* 384:417–431 and Harris et al. (1987) *Respiration Physiology: A Quantitative Approach*, Chang and Pavia, editors, Dekker, New York, in press. This method has great advantages in its measurement accuracy; however, it has the disadvantage of analytical complexity and requires the use of radioactive materials.

As discussed in the previously cited works, Harris et al. have shown that $^{14}C$-urea is useful in the measurement of lung vascular PS. However, this radioactive substance cannot be measured by optical means. Harris et al. *J. Appl. Physiol.* (1987) 62:1852–1859, 1987 have shown that propanediol is virtually identical to urea in its ability to measure alterations in P. S. Galloway et al. (1986) *Proc. 39th Ann. Conf. of the Engineering Medicine and Biology Society*, 28:157 have shown that the infrared spectral signature of propanediol was such that it could be easily measured in trace quantities in whole blood.

SUMMARY OF THE INVENTION

Infrared sensitive indicator-dilution tracers, specifically, 1,2 propanediol, can be optically measured from blood drawn from the systemic arterial system to indicate lung vascular function and transcapillary transport. Further, red cells containing sulfur-labelled hemoglobin may be added to the nonradioactive indicator mixture and measured by absorption of visible light to aid in the extravascular lung water and PS measurements.

DETAILED DESCRIPTION

1. Introduction

Figure 1:
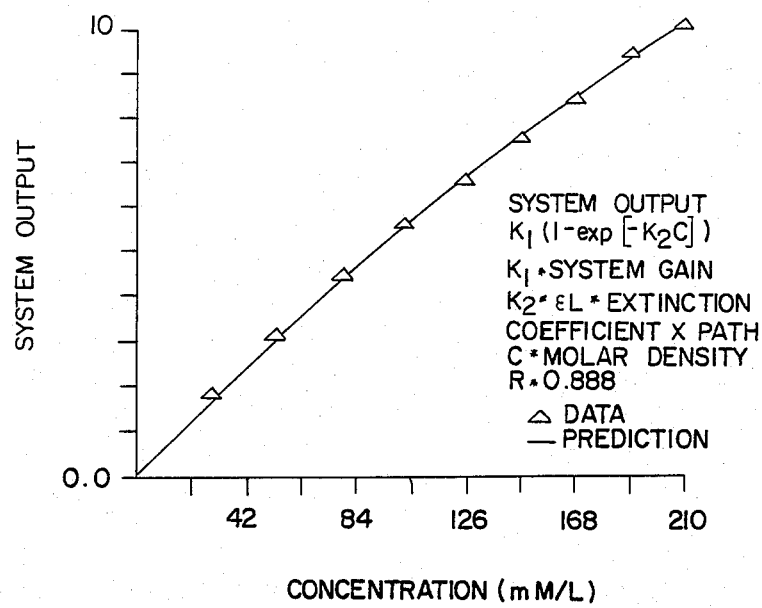
FIG. 1 is a calibration curve for 1,2-propanediol as a function of Miran system output.

Optical measurement used in the indicator-dilution method is superior to the radioisotope measurements in that more studies are possible when no radioactivity is present. Further, the use of microcomputers with the optical measurement provides for the immediate analysis of the sample. Thus, the state of the microvasculature may be tracked in time in experimental animals and patients with greater ease than using radioisotope measurements. Further, optical methods improve sampling speed and accuracy.

The present invention relates to the optical detection utilizing infrared spectroscopy of 1,2-propanediol, a tracer sensitive to permeability changes in the lung.

Indicator-dilution tracers, such as indocyanine green dye, red cells labelled with sulfhemoglobin, deuterated water and preferably 1,2-propanediol can be admixed for injection into the circulatory system. Each quantity can also be injected individually and compared mathematically.

2. Procedure for Measuring Lung Vascular Function

Arterial blood is withdrawn from an indwelling arterial catheter and passed through a rotary pump which is part of the analysis device. Blood moves at approximately 1 ml/sec. through a series of optical chambers. The absorption properties of light at differing wavelengths are sensed by specially selected detectors. A brief period is used to achieve a baseline observation of light absorption in each channel. Then a mixture of the subject's own blood which has been labelled with hydrogen sulfide (3 ml) is combined with 5 to 5 ml of 1,2-propanediol, 1 to 2 ml of indocyanine green dye, 2–3 ml of deuterated water. Three to 5 ml of this mixture is then rapidly injected as a bolus through an indwelling catheter with its distal end in the lumen of the right artrial or right ventricular chamber.

Arterial blood is again sampled through the systemic arterial line and the blood stream is interrogated for absorption of light at specific wavelengths. The microcirculatory properties of the lung cause variations in the tracer concentrations. The resulting concentration changes are measured with optical detectors, converted to electronic signals, acquired in digital form and, in the integrated microcomputer, converted to standard indicator dilution curves by normalizing concentration to the amount of tracer injected. A separate concentration-time curve is produced for each indicator a total of four-sulfhemoglobin red cells, indocyanine green dye, deuterated water and 1,2-propanediol. Then, mathematical analysis is used to compare the curves. Theory from the scientific literature (Harris, T. R., and Brigham, K. L. (1982). *Ann. N.Y. Acad. Sci.*, 384:417–434.; Harris et al., *J. Appl. Physiol.* 62, 1852–1859, 1987) is used to compute (within a program resident on the microcomputer) the following quantities: 1. pulmonary blood flow; 2. pulmonary intravascular volume; 3. extravascular water volume; 4. microcirculatory permeability-surface area (PS) for 1,2-propanediol. These parameters are displayed after calculation and are available for physician interpretation of the status of the lung microcirculation at the time of study. In this manner, microvascular permeability-surface are and other microcirculatory parameters can be simultaneously monitored in intensive care or other patient populations.

3. Basis of Concentration Measurements

Beer's Law can be used to relate concentrations of a material (tracer) dissolved in a background substance (blood) in the following manner:

The light intensity transmitted to the detector for a pure background material ($I_b$) is $$I_b = I_0 S_b \exp[-\epsilon_b C_b L] \quad [1]$$

where $\epsilon_b$ is background material extinction coefficient, $S_b$ is the backscattering term, $C_b$ is molar density of the background material, L is the optical path length and $I_0$ is the intensity of incident light.

For a mixture of background and tracer in a material with backscattering such as a whole blood:

$$I_M = I_0 S_m \exp\{-[(1-f_T)\epsilon_b C_b + f_T \epsilon_T C_T]L\} \quad [2]$$

where $I_M$ is a mixture transmitted intensity, $f_t$ is mole fraction of tracer in the mixture, $\epsilon_T$ is extinction coefficient of tracer, $C_T$ is molar density of tracer and $S_m$ is a complex function characterizing back scattering in the blood-tracer mixture.

Thus, $$\text{Log}(I_b/I_0) = -\epsilon_b C_b L - B_b \quad [3]$$

$$\text{Log}(I_M/I_0) = -[(1-f_T)\epsilon_b C_b + f_T \epsilon_T C_T]L - B_m \quad [4]$$

where $B_b$ and $B_m$ are backscattering terms resulting from the logarithmic transformations of $S_b$ and $S_m$.

Subtracting equation [3] from equation [4] yields $$-\text{Log}[I_M/I_b] = f_T[\epsilon_T C_T - \epsilon_b C_b]L + [B_m - B_b] \quad [5]$$

Usually, $B_m$ approximates $B_b$ and back scattering effects disappear. In this way a logarithmic relationship is seen to exist between the relative intensity change due to a mixture, the tracer fraction and basic material properties ($\epsilon_b$, $\epsilon_T$, $C_b$, $C_T$). The quantity $f_T$ is the desired measure of tracer concentration which can be analyzed mathematicaly. Further, detected I is related to instrument design features through the choice of window length L and the electronic gains of the circuits which acquire the detector outputs. The choice of tracer and spectrum window is dictated by the need to maximize the material factor $\epsilon_T C_T - \epsilon_b C_b$.

An example of calibration based on this process is shown in FIG. 1 where the system output of the detector circuit (in arbitrary electronic units) is shown as a function of 1,2-propanediol concentration in normal physiological saline.

4. Instrument Design

The individual cells used in this project are simple non-adjustable monochromators. These devices have seen considerable use and the constraints in the design of the devices are discussed by Conn and Avery [(1960). *Infrared methods: Principles and Applications*, New York, Academic Press].

Figure 2:
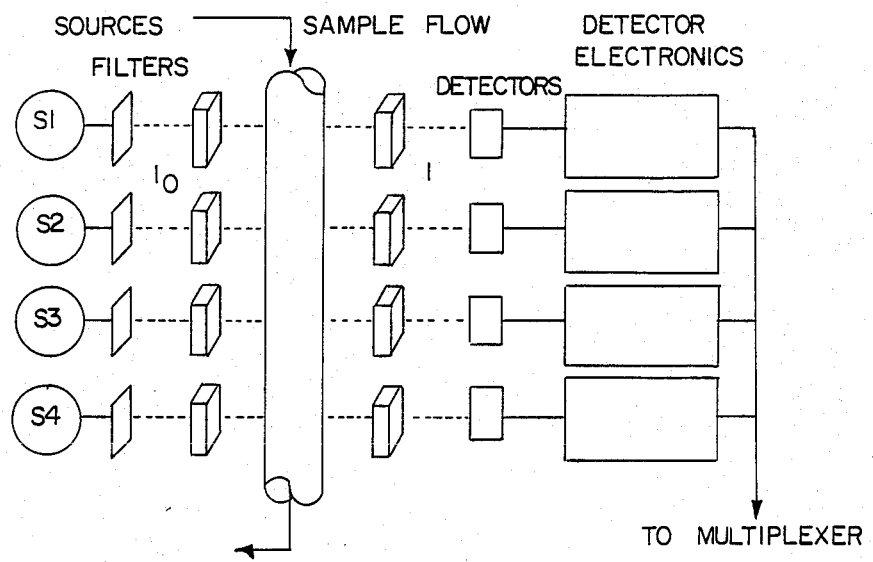
FIG. 2 is a schematic diagram of the multichannel optical measuring system.

In the present invention, both visible and infrared light are used to probe for indicator concentrations. The arrangement consists of a sequence of flow-through cells, each having its own, specific interrogation frequency. This arrangement is shown in FIG. 2.

By designing the system as a sequence of separate chambers, each cell, source and detector is matched for the frequency of interest.

Figure 3:
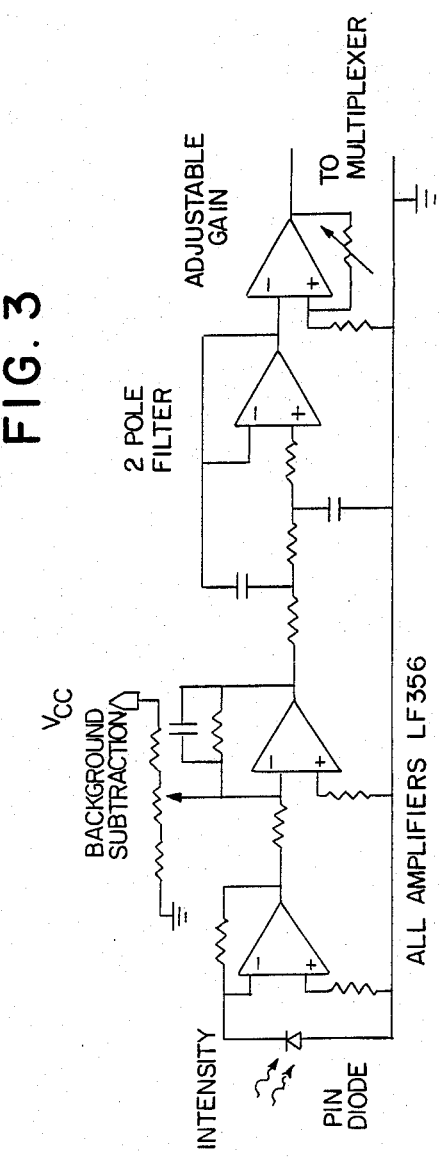
FIG. 3 is a schematic diagram of a circuit for conditioning output from optical detectors.

Each source provides a broadband illumination from which the narrowband intensity $I_0(2)$ is selected by the optical filter. This interrogation intenstiy passes through the near wall of a flow cell and into the flow-sampled blood. The emergent intensity (I) passes out of the blood and falls on a detector selected for the optimum response for that wavelength. A differential circuit subtracts a background-equivalent reference voltage from the detector signal and the difference is amplified. This signal is electronically filtered and the filtered signal is sent into a multiplexer. A schematic of the electronics for signal conditioning for a channel is shown in FIG. 3. The multiplexer, under computer control, selects each wavelength channel in turn and the signals are digitized, displayed and saved for later analysis.

The following choices of sources, windows and detectors are embodied in the present invention:

(a) ICG Channel: A commercial standard of a tungsten source and an 800 nanometer filter are used to provide the initial intensity. The filter is a stock (Infrared Industries) filter with a half power width of 10 nm. This provides more than adequate separation from the 620 nm channel. The flow cell is quartz with 0.2 mm optical pathlength. The emergent intensity is detected by a Hewlett-Packard 5082-4207 PIN diode.

(b) Sulfhemoglobin Channel: A tungsten source is also used to provide the initial intensity but here a 620 nm filter is used to select the wavelength of interest. The cell and detector are a quartz cell and PIN diode detector.

(c) $D_2O$ Channel: a black-body radiator is appropriate for generating a signal. A blackened cavity is heated by a ceramic slug wrapped by a nichrome wire. The walls of the cavity absorb the energy from the nichrome and ceramic and radiate out a signal in infrared wavelengths. The magnitude and frequency spectra of the radiated signal are functions of the temperature to which the cavity is raised. The temperature can be controlled by controlling the current through the nichrome wire. An operating temperature of 1200° C. provides peak intensity at 4.0 microns. A 4.0 micron wavelength filter (Infrared Industries) is used to narrow the interrogation bandwidth.

The cell material for the $D_2O$ channel is calcium fluoride. This material is acid resistant, has a good index of hardness and is transparent (>80%) in the 4.0 micron wavelength. The detector choice is the photon-sensitive lead selenide.

(d) Propanediol Channel: The source is a cavity radiator with a temperature in the 1200°-2000° C. range. Filters are used to eliminate extraneous energy and provide a narrow band centered at 9.1 microns.

The material for the flow cell is zinc selenide. It has good transmission characteristics, is insoluble in water and has excellent hardness (178 knoops). A thermopile detector (Barnes 1-M) is used to capture the transient concentration signal.

5. Software Design

Figure 4:
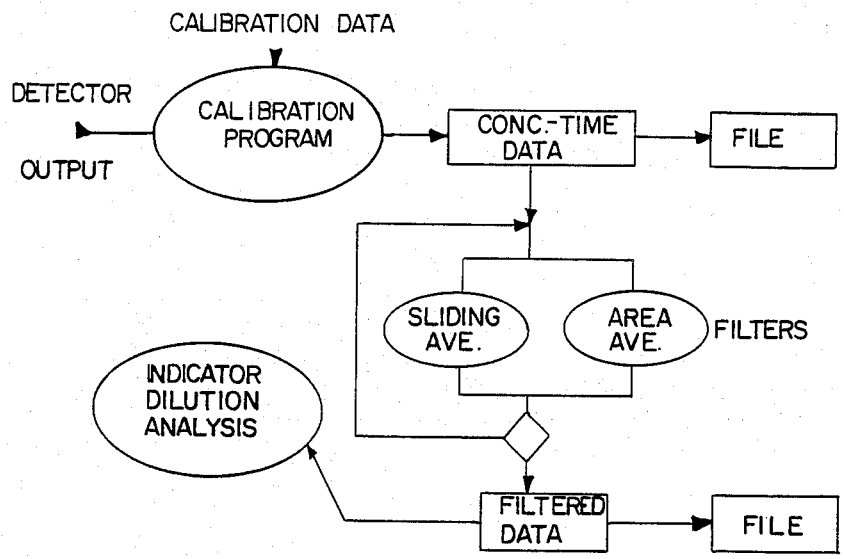
FIG. 4 is a schematic diagram of the signal acquisition software for the optical device.

A microcomputer with a graphics card and an A to D Converter for signal acquisition and analysis is suitable for use with the present invention. The software consists of two kinds of calculation: (1) signal acquisition, calibration and filtering software; (2) indicator-dilution curve analysis. The first of these systems is diagrammed in FIG. 4. A light detector output signal is utilized to calculate concentration for known calibrations. This provides a raw concentration-time curve which is filtered with simple sliding or area averaging. This procedure results in a smoothed concentration time curve.

Indicator curve analysis is performed using the methods of Harris et al. infra.

EXAMPLE I

Figure 5:
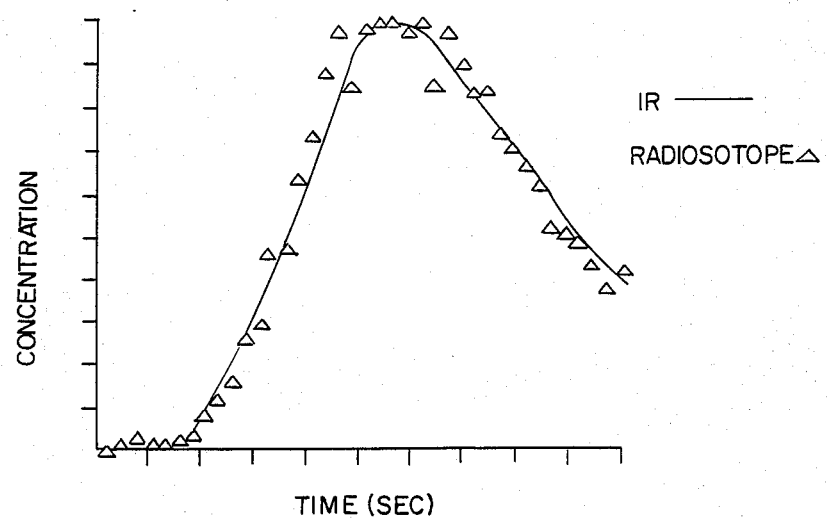
FIG. 5 is the results of the comparison of $^{14}C$-1, 2-propanediol indicator curve to IR measured 1,2-propanediol curves from isolated plasma-perfused dog lung.
Figure 6A:
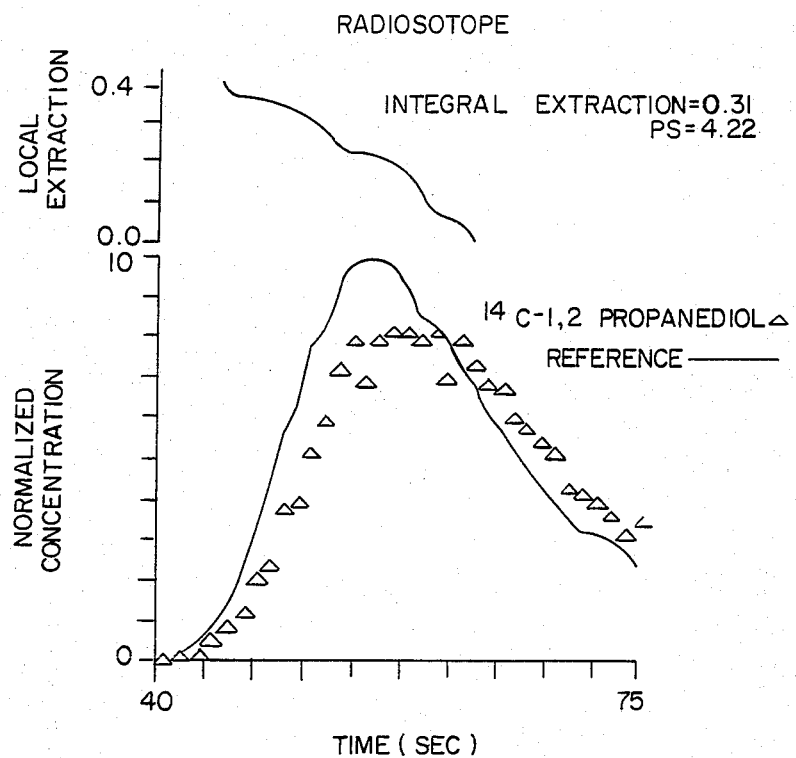
FIG. 6A is the graphic comparison of radioisotope indicator curves for 1,2 propanediol from isolated perfused dog lung.
Figure 6B:
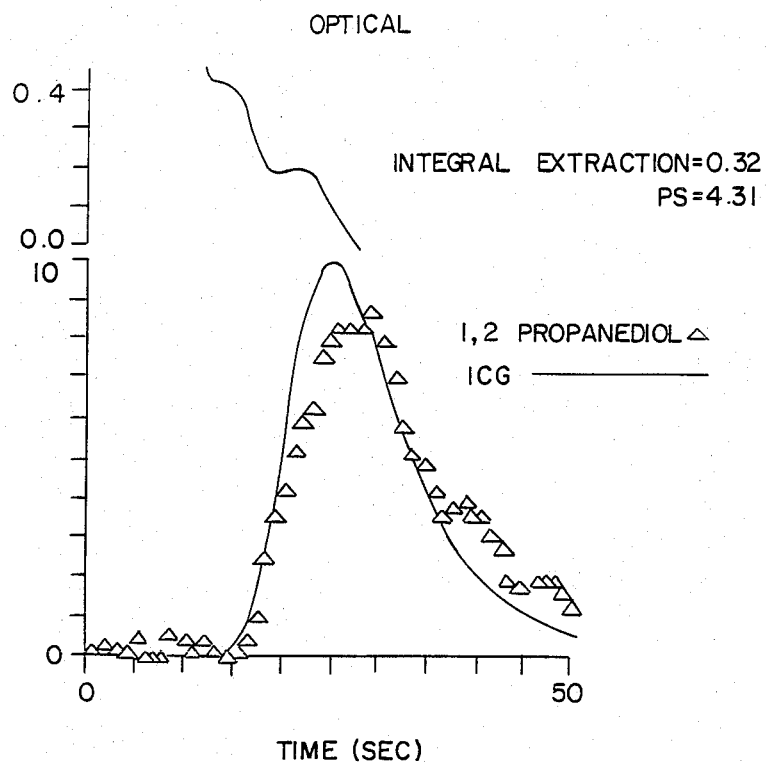
FIG. 6B is the graphic comparison of optical indicator curves for 1,2 propanediol from isolated perfused dog lung.

The optical device previously described was used to measure indicator dilution curves for 1,2-propanediol in an isolated plasma-perfused dog lung experiment under baseline conditions and after infusion of alloxan to cause lung injury. The optical curves were compared to radioisotope curves using $^{14}C$-1, 2-propanediol. Indocyanine green dye reference curves were also measured. The optical methods have a greater frequency response than the isotope sampling system. The transfer function between the dye curve machine, the IR sensor and the isotope collection system was also determined. The optical curve was corrected by convoluting it with the IR-to-isotope sampler transfer function and compared it with the isotope curve. Excellent agreement was found as is shown in FIG. 5. In addition, agreement with extraction pattern and PS for 1,2 propanedol was also excellent (FIGS. 6a and 6b). These studies show the feasibility of the optical methods to measure lung parameters.

6. Sulfhemoglobin as a Red Cell Marker

In the measurement of lung vascular PS by isotope methods, we have found that tracers sensitive to vascular injury such as urea and propanediol also undergo red cell carriage. Usually this phenomenon may be corrected by including a red cell label in the indicator mixture (Parker, R. E., Roselli, R. J., Haselton, F. R. and Harris, T. R. *J. Applied Physiol.* 60:1203-1299, 1986.). Red cells labelled with sulfur, with concentrations measured optically, could act as a nonradioactive marker of red cell transit in an indicator mixture. Such an application in a microcirculatory experiment has been published by Baker et al. (*Am. J. Physiol.*, 238:H745-H749, 1980).

Red cells marked with sulfhemoglobin (S-rbc) have an absorption peak which allows easy differentiation from other hemoglobins (Van Kampen, E. J., and Zijlstra, W. G. (1983). *Adv. in Clin. Chem.*, 23:199-257.) and from indocyanine green dye (Mook et al. (1979) *Cardiovascular Res.*, 13:233-237). Further, Baker et al. have shown that mixtures of sulfhemoglobin labelled red cells and normal red cells form a linear relationship between the fraction of S-rbcs and optical absorption at 620 nm. These investigators used the S-rbcs as labels of red cell transit in microcirculatory experiments. In the present invention, the utility of S-rbcs is novel in that they are used as a red cell marker in a multiple indicator mixture which flows through the entire lung circulation.

S-rbcs are prepared in the following manner: Fresh whole blood from the subject is centrifuged and the cells removed and resuspended in physiological saline. Then, the suspension is passed through a fiber and tube clinical hemodialyser with hydrogen sulfide gas introduced into the shell side. When the solution reaches a greenish color, the mixture is removed and centrifuged. Then, cells are washed three times to remove residual $H_2S$, resuspended to the original hematocrit and mixed by volumetric dilution to form tracer mixtures. We have found this procedure to be straightforward and nondestructive of red cells.

Figure 7:
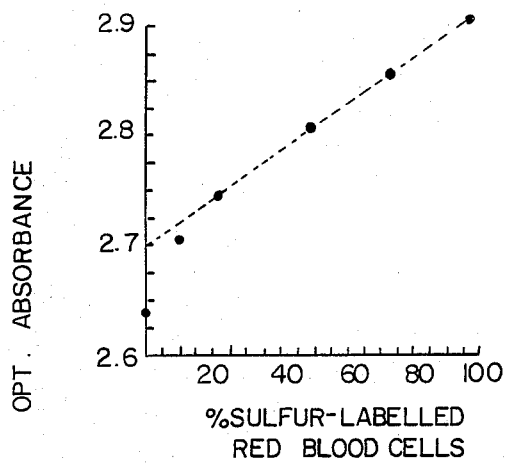
FIG. 7 is the optical absorbance of mixed blood as a function of volume fraction of $H_2S$ exposed blood.

Partial solutions of sulfhemoglobin-blood have been formed by mixing normal blood with even aliquots of $H_2S$-exposed blood. The sulfhemoglobin content of the resulting mixture was determined in the whole blood using a Hewlett-Packard HP8450AUV/VIS spectrometer to analyze the true sulfhemoglobin content. The results are shown in FIG. 7 where a linear relation between the volume of exposed blood and the visible light absorbance is seen. This indicates that blood labelled in this manner will likely be a useful marker of red cell transit when absorbance is measured at 620 nanometers.

The methods performed in the Harris, et al., *J. Appl. Physiol.*, 62:1852-1859 (1987) are further described:

MATHEMATICAL ANALYSIS OF INDICATOR-DILUTION CURVES

The optical density measurements discussed above lead to a set of normalized indicator dilution curves of sulfhemoglobin red blood cells, ICG-labelled albumin, 1,2-propanediol and $D_2O$. After normalization, the natural logarithm of the concentration-time curves is calculated. Several points are selected and extrapolated to compute the area under each curve. Extrapolation is selected to give the best fit to the selected points and to provide the closest match among curve areas. Both criteria must be satisfied. Curves failing to achieve a ratio of 1.00±0.05 to the area of the ICG-albumin curve are rejected.

Flow rate of water through the lungs, $F_w$, is computed from total blood flow and hematocrit (Hct.) by the equation suggested by Goresky, et al., *J. Clin. Invest.*, 48:487-501 (1969):

$$F_w = \{0.7 \, (Hct.) + 0.94 \, (1 - Hct.)\} \text{ Total blood flow} \quad (A)$$

Total blood flow is determined by application of the Stewart-Hamilton formula to the ICG-albumin curves. A composite intravascular reference concentration, against which escape of D₂O and 1,2-propanediol are measured, is calculated by the following equation (Goresky, et al., *J. Clin. Invest.*, 48:487-501 (1969):

$$C_R = \frac{0.7(\text{Hct.})(\text{sulfhemoglobin-red cell conc.}) + 0.94(1 - \text{Hct.})(\text{ICG-albumin conc.})}{0.7 \text{ Hct.} + 0.94(1 - \text{Hct.})} \quad (B)$$

This accounts for the fact that within the vascular space, urea and water are in both the red cell and plasma phases (Goresky, et al., *J. Clin. Invest.*, 48:487-501 (1969); Parker, et al., *J. Appl. Physiol.*, 60:1293-1299 (1986).

We considered labelled water to be entirely flow limited in the lung. The mean transit times for labelled water ($t^-D2O$) and $CR(t^-REF)$ are computed by the equation:

$$\bar{t} = \frac{\int_0^\infty tC\,dt}{\int_0^\infty C\,dt} \quad (C)$$

the extravascular water volume is computed as:

$$V_e = F_w \times (t^-_{D2O} - t^-_{REF}) \quad (D)$$

The instantaneous extraction of urea ($C_D$) is computed as:

$$E(t) = 1 - \frac{C_D(t)}{C_R(t)} \quad (E)$$

where $C_D(t)$ is the normalized 1,2-propanediol tracer concentration.

The integral extraction for 1,2-propanediol ($E_i$) is computed as:

$$E_i = \frac{\int_0^{t_p} (C_R - C_D)\,dt}{\int_0^{t_p} C_R\,dt} \quad (F)$$

by Simpson's rule. The term $t_p$ is the time at which the peak of the reference curve appears.

Extraction PS is computed as:

$$PS = -F_w \log_e(1 - E_i) \quad (G)$$

This equation neglects from the extravascular space. A model correcting this omission is discussed below.

An alternative to equation [G] is the use of a mathematical model based on tracer capillary flow and diffusion. The capillary concentrations of permeating tracers were considered to be described by the solution to equations which allow one-dimensional convection with a distributed loss of material as shown below.

$$\frac{\partial C_D}{\partial t} + \frac{F_c}{V_c} \frac{\partial C_D}{\partial X'} = -N \quad (H)$$

where $F_c$ is capillary blood flow, N is the rate of loss of material by transcapillary exchange, t is time; $X'$ is distance from the capillary entrance normalized to total capillary length; and $V_c$ is intracapillary blood volume.

A similar equation holds for the reference indicator, $C_R$, except that N is zero.

$$\frac{\partial C_R}{\partial t} + \frac{F_c}{V_c} \frac{\partial C_R}{\partial X'} = 0 \quad (I)$$

We use a model for N proposed by Haselton, et al., *J. Appl. Physiol.*, 57:98-109 (1984) in which N is considered to be a diffusional flow across the capillary barrier and into the extravascular space. N is described by the equation:

$$N = \frac{-SD}{V_{cap}} \frac{\partial C_D'}{\partial y'} \bigg|_{y' = 0} \quad (J)$$

where D is the equivalent of tracer in the extraluminal space and S is microvascular transport surface area. The variation of $C_D'$ with time and position in the extravascular space, $y'(yL_e$, the extravascular diffusion distance) is given by the equation:

$$\frac{\partial C_D'}{\partial t} = \frac{D}{L_e^2} \frac{\partial^2 C_D'}{\partial y'^2} \quad (K)$$

where $C_D'(0,x,y) = 0 \; C_D' = (t,x,\infty) = 0$

Equations [H] and [K] are solved and fitted to experimental 1,2-propanediol curves by methods discussed by Haselton, et al., *J. Appl. Physiol.*, 57:98-109 (1984).

The entire indicator analysis yields PS for 1,2-propanediol, D½S for 1,2-propanediol and $V_e$, the extravascular lung water volume. The parameter D is equivalent diffusivity which includes the effects of all extravascular diffusion resistances.

Equation 3 is also used to estimate intracapillary blood volume. The quantity $t^-_{REF}$ is reduced by the appearance time, ($t_{app}$), and an intravascular volume, $V_v$, is computed from the equation:

$$V_v = F_w \times (t^-_{REF} - t_{app}) \quad (L)$$

These parameters (PS, $V_e$, $F_w$, $V_v$) have been shown to be useful in characterizing the microvascular damage of the Adult Respiratory Syndrome (Brigham, et al., *J. Clin. Invest.*, 72:339-349 (1983).

The present invention may be embodied in other specific forms without departing from the spirit or essential attributes thereof and, accordingly, reference should be made to the appended claims, rather than to the foregoing specification, as indicating the scope of the invention.

We claim:

1. An indicator dilution method for measuring lung vascular function, said method comprising:
   injecting an indicator mixture which comprises 1, 2 propanediol into the circulatory system so that the mixture becomes diluted with blood,
   withdrawing a sample of arterial blood,
   measuring the transmittance of filtered light through the blood.

2. The method of claim 1 wherein the filtered light is measured by infrared absorbance.

3. The method of claim 1 wherein the indicator mixture comprises red blood cells labelled with sulfhemoglobin.

4. The method of claim 1 wherein the indicator mixture is present in an amount effective for measuring transmitted, filtered light at 0.800 microns, 0.620 microns, 4.0 microns and 9.1 microns for determining lung vascular function.

5. A method of measuring microcirculatory changes caused by Adult Respiratory Distress Syndrome, said method comprising:
   injecting 1, 2 propanediol in an indicator mixture which may be comprised of ingredients selected from the group consisting of indocyanine green dye, red blood cells labelled with sulfhemoglobin and deuterated water into the circulatory system so that the mixture becomes diluted with blood,
   withdrawing a sample of arterial blood, and
   measuring the transmittance of filtered light through the blood,
   determining the relative concentrations of each ingredient in said indicator mixture, and
   computing parameters characteristic of lung microvascular function.

6. The method of claim 5 wherein the indicator mixture in an amount effective for measuring transmitted filtered light at 0.800 microns, 0.62 microns, 4.0 microns and 9.1 microns for determining lung vascular function.

7. An indicator dilution method for measuring lung vascular function, said method comprising:
   injecting an indicator mixture which comprises 1, 2 propanediol and an ingredient selected from the group consisting of indocyanine green dye, red blood cells labelled with sulfhemoglobin and deuterated water into the circulatory system so that the mixture becomes diluted with blood,
   withdrawing a sample of arterial blood,
   measuring the transmittance of filtered light through the blood.

8. The method of claim 7 wherein the indicator mixture is present in an amount effective for measuring transmitted filtered light at 0.800 microns, 0.62 microns, 4.0 microns and 9.1 microns for determining lung vascular function.

* * * * *